United States Patent
Xu et al.

(10) Patent No.: US 7,893,064 B2
(45) Date of Patent: Feb. 22, 2011

(54) HYDRAZONE DERIVATIVES AS KINASE INHIBITORS

(75) Inventors: Guozhang Xu, Bensalem, PA (US); Lily Lee Searle, Waltham, MA (US); Shenlin Huang, San Diego, CA (US)

(73) Assignee: Janssen Pharmaceutica NV (BE)

( * ) Notice: Subject to any disclaimer, the term of this patent is extended or adjusted under 35 U.S.C. 154(b) by 691 days.

(21) Appl. No.: 11/871,472

(22) Filed: Oct. 12, 2007

(65) Prior Publication Data

US 2008/0114004 A1   May 15, 2008

Related U.S. Application Data

(60) Provisional application No. 60/855,721, filed on Oct. 31, 2006.

(51) Int. Cl.
  *C07D 403/12* (2006.01)
  *A61K 31/506* (2006.01)
(52) U.S. Cl. .................. 514/235.8; 514/252.19; 514/256; 544/122; 544/295; 544/328
(58) Field of Classification Search .............. 544/122, 544/295, 328; 514/235.8, 252.19, 256
See application file for complete search history.

(56) References Cited

U.S. PATENT DOCUMENTS

| 6,727,256 B1 | 4/2004 | Carter et al. |
| 2005/0215553 A1 | 9/2005 | Bhatnagar et al. |

OTHER PUBLICATIONS

Ulrich, Chapter 4: Crystallization, Kirk-Othmer Encyclopedia of Chemical Technology, pp. 1-7, Aug. 2002.*
Vippagunta et al., Cyrstalline Solids, Advanced Drug Delivery Reviews, 48, pp. 3-26, 2001.*
West, Solid Solutions, Solid State Chemistry and its applications, pp. 358 & 365, 1988.*
Layzer, Degenerative Diseases of the Nervous System, Cecil Textbook of Medicine, 20th Edition, vol. 2, 2050-7, 1996.*
Banker et al., Prodrugs, Modern Pharmaceutics, Third Edition, Revised and Expanded, pp. 451 and 596, 1996.*
Bundgaard, Design of Prodrugs, p. 1, 1985.*
Wolff, Some consideration for prodrug design, Burger's Medicinal Chemistry and Drug Discovery, 5th edition, vol. I: Principles and Practice, pp. 975-977, 1995.*
Traxler, Protein Tyrosine Kinase Inhibitors in cancer treatment, Expert Opinion on Therapeutic patents, 7(6):571-588, 1997.*
Simone, Oncology: Introduction, Cecil Textbook of Medicine, 20th Edition, vol. 1, pp. 1004-1010, 1996.*
Fabbro et al., Protein kinases as targets for anticancer agents: from inhibitors to useful drugs, Pharmacology & Therapeutics 93, pp. 79-98, 2002.*
Douglas, Jr., Introduction to Viral Diseases, Cecil Textbook of Medicine, 20th Edition, vol. 2, pp. 1739-1747, 1996.*
Damasio, Alzheimer's Disease and Related Dementias, Cecil Textbook of Medicine, 20th Edition, vol. 2, 1992-6, 1996.*
International Search Report dated Mar. 10, 2008 for International Appln. No. PCT/US2007/21923.

* cited by examiner

*Primary Examiner*—Deepak Rao

(57) ABSTRACT

The present invention is directed to novel bicyclic pyrimidine compounds of Formula (I) or a form or composition thereof

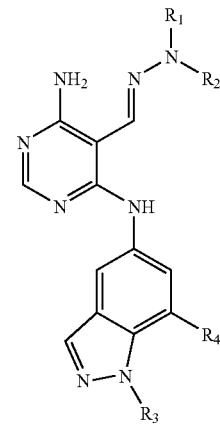

as inhibitors of ATP-protein kinase interactions, wherein substituents on each side of the iminomethyl double bond in Formula (I) may be in the E or Z configuration; and wherein $R_1$, $R_2$, $R_3$ and $R_4$ are as defined herein.

22 Claims, No Drawings

HYDRAZONE DERIVATIVES AS KINASE INHIBITORS

CROSS REFERENCE TO RELATED APPLICATIONS

This application claims priority of the filing date of U.S. Provisional application Ser. No. 60/855,721 filed Oct. 31, 2006, entitled "Hydrazone Derivatives as Kinase Inhibitors," the entire disclosures of which are hereby incorporated by reference into the present disclosure.

FIELD OF THE INVENTION

The present invention is in the area of novel bicyclic substituted pyrimidine compounds or forms thereof, their synthesis and their use as kinase inhibitors.

BACKGROUND OF THE INVENTION

In general, protein kinases are the largest set of structurally related phosphoryl transferases, have highly conserved structures and catalytic functions and may be categorized into families by the substrates they phosphorylate (e.g., protein-tyrosine, protein-serine/threonine, histidine and the like) and are responsible for the control of a wide variety of cellular signal transduction processes.

Protein kinases catalyze and regulate the process of phosphorylation. Phosphorylation modulates or regulates a variety of cellular processes such as proliferation, growth, differentiation, metabolism, apoptosis, motility, transcription, translation, and other signaling processes. Uncontrolled signaling for cell growth due to defective control of protein phosphorylation has also been implicated in a number of diseases.

Phosphorylation modulates or regulates a variety of cellular processes such as proliferation, growth, differentiation, metabolism, apoptosis, motility, transcription, translation and other signaling processes. Defective control of protein phosphorylation due to unregulated cellular mitosis, unregulated cell proliferation and upregulated kinase activity has been implicated in a number of diseases and disease conditions, such as osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases. Therefore, kinase inhibitors have potential use as therapeutic agents.

There is a need for potent small-molecule kinase inhibitors of one or more of the EGFR or HER2 kinase proteins and the like possessing anti-tumor cell proliferation activity, and as such are useful for treating a EGFR or HER2 kinase receptor mediated, angiogenesis-mediated or hyperproliferative disorders.

SUMMARY OF THE INVENTION

The present invention is directed to novel compounds of Formula (I) or a form thereof:

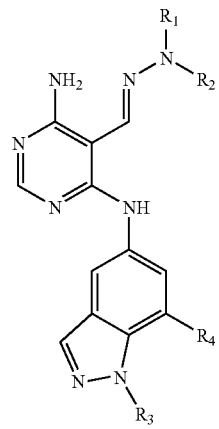

as inhibitors of ATP-protein kinase interactions, wherein substituents on each side of the iminomethyl double bond in Formula (I) may be in the E or Z configuration; and wherein $R_1$, $R_2$, $R_3$ and $R_4$ are as defined herein.

Embodiments of the present invention include a composition or medicament comprising one or more compounds of Formula (I) or a form thereof.

The present invention includes a method of synthesizing compounds of Formula (I) or a form thereof.

The present invention includes the use of one or more compounds of Formula (I) or a form thereof as protein kinase inhibitors, wherein the protein kinases include serine/threonine kinases and tyrosine kinases.

Examples of the present invention include protein kinases selected from EGFR and HER2, wherein the compounds of Formula (I) or a form thereof are useful for preventing, treating or ameliorating chronic or acute kinase mediated diseases.

Embodiments of kinase-mediated diseases include an EGFR protein kinase mediated cytomegalovirus (CMV) infection. In a related embodiment, the compounds of Formula (I) or a form thereof are useful contraceptive agents.

The present invention is further directed to a method for ameliorating, treating or preventing a chronic or acute kinase mediated disease in a patient in need thereof comprising administering to the patient an effective amount of one or more compounds of Formula (I) or a form thereof.

Embodiments of the present invention include a chronic or acute disease mediated by a kinase selected from EGFR and HER2.

An aspect of the method includes inhibiting unregulated kinase activity in the patient, as well as unregulated kinase expression or signaling, unregulated expression or signaling of a kinase selected from EGFR and HER2 and unregulated expression or signaling which results in unregulated cell proliferation. Such unregulated cell proliferation includes cancer, metastatic cancer cell invasion or metastatic cancer cell migration. Cancer further includes tumors mediated by the unregulated activity of kinases selected from EGFR and HER2, including non-small-cell lung cancers, colon cancers, breast cancers and the like. An aspect of the method also includes an amount of one or more compounds of Formula (I) or a form thereof, which is effective to induce remission of a chronic form of a cancer. Such an amount includes an amount, which is effective at a low dose to inhibit unregulated kinase activity.

The present invention includes the use of one or more compounds of Formula (I) or a form thereof in the preparation of a composition or medicament for preventing, treating or ameliorating chronic or acute kinase mediated diseases.

These and other aspects and advantages of the invention, which will become apparent in light of the detailed description below, are achieved through use of the compounds of this invention.

DETAILED DESCRIPTION OF THE INVENTION

The present invention provides bicyclic pyrimidine compounds of Formula (I):

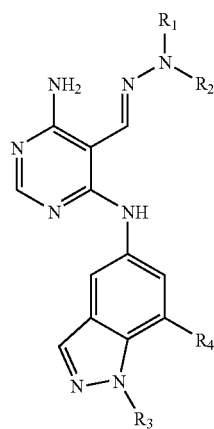

and a form thereof, wherein substituents on each side of the iminomethyl double bond in Formula (I) may be in the E or Z configuration; and wherein $R_1$ is hydrogen, $C_{1-6}$alkyl, trihalo $C_{1-6}$alkyl, $C_{3-6}$cycloalkyl, optionally substituted phenyl, or optionally substituted benzyl, wherein phenyl and the phenyl portion of benzyl is optionally substituted with one, two or three substituents selected from $C_{1-6}$alkyl, $C_{1-6}$alkoxy, hydroxy, amino, halogen, or trihalo $C_{1-6}$alkyl;

$R_2$ is hydrogen, or $C_{1-6}$alkyl;

or $R_1$ and $R_2$ taken together form an optionally substituted heterocyclic ring, wherein the heterocyclic ring is optionally substituted with one, two or three substituents selected from $C_{1-6}$alkyl, $C_{1-6}$alkoxy, $C_{1-6}$alkoxy-$C_{1-6}$alkyl, hydroxy-$C_{1-6}$alkyl, or trihalo $C_{1-6}$alkyl;

$R_3$ is benzyl optionally substituted with halo; and $R_4$ is hydrogen or halo.

An example of the present invention is a compound of Formula (I) and a form thereof wherein $R_1$ is hydrogen, $C_{1-4}$alkyl, trihalo $C_{1-4}$alkyl, optionally substituted phenyl, or optionally substituted benzyl, wherein phenyl and the phenyl portion of benzyl is optionally substituted with one, two or three substituents selected from $C_{1-4}$alkyl, $C_{1-4}$alkoxy, hydroxy, amino, halogen, or trihalo $C_{1-4}$alkyl.

An example of the present invention is a compound of Formula (I) and a form thereof wherein $R_1$ is hydrogen, $C_{1-4}$alkyl, trihalo $C_{1-4}$alkyl, or optionally substituted phenyl, wherein phenyl is optionally substituted with one, two or three substituents selected from $C_{1-4}$alkyl, $C_{1-4}$alkoxy, hydroxy, amino, halogen, or trihalo $C_{1-4}$alkyl.

An example of the present invention is a compound of Formula (I) and a form thereof wherein $R_1$ is $C_{1-4}$alkyl, trihalo $C_{1-4}$alkyl, or phenyl substituted with $C_{1-4}$alkoxy.

An example of the present invention is a compound of Formula (I) and a form thereof wherein $R_1$ and $R_2$ taken together form an optionally substituted heterocyclic ring, wherein the heterocyclic ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl.

An example of the present invention is a compound of Formula (I) and a form thereof wherein $R_1$ and $R_2$ taken together form an optionally substituted pyrrolidinyl, morpholinyl, piperidinyl or piperazinyl ring, wherein the pyrrolidinyl, morpholinyl, piperidinyl or piperazinyl ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl.

An example of the present invention is a compound of Formula (I) and a form thereof wherein $R_1$ and $R_2$ taken together form an optionally substituted pyrrolidinyl, morpholinyl, piperidinyl or piperazinyl ring, wherein the pyrrolidinyl or piperazinyl ring is optionally substituted with one substituent selected from $C_{1-4}$alkyl, $C_{1-4}$alkoxy-$C_{1-4}$alkyl, hydroxy-$C_{1-4}$alkyl.

An example of the present invention is a compound of Formula (I) and a form thereof wherein $R_2$ is hydrogen.

An example of the present invention is a compound of Formula (I) and a form thereof wherein $R_2$ is $C_{1-4}$alkyl.

An example of the present invention is a compound of Formula (I) and a form thereof wherein $R_3$ is benzyl substituted with halo.

An example of the present invention is a compound of Formula (I) and a form thereof wherein $R_4$ is hydrogen.

An example of the present invention is a compound of Formula (I) and a form thereof wherein $R_1$ is hydrogen, $C_{1-4}$alkyl, trihalo $C_{1-4}$alkyl, optionally substituted phenyl, or optionally substituted benzyl, wherein phenyl and the phenyl portion of benzyl are optionally substituted with one, two or three substituents selected from $C_{1-4}$alkyl, $C_{1-4}$alkoxy, hydroxy, amino, halogen, or trihalo $C_{1-4}$alkyl;

$R_2$ is hydrogen, or $C_{1-4}$alkyl;

or $R_1$ and $R_2$ taken together form an optionally substituted heterocyclic ring, wherein the heterocyclic ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl;

$R_3$ is benzyl optionally substituted with halo; and $R_4$ is hydrogen.

An example of the present invention is a compound of Formula (I) and a form thereof wherein $R_1$ is hydrogen, $C_{1-4}$alkyl, trihalo $C_{1-4}$alkyl, or optionally substituted phenyl, wherein phenyl is optionally substituted with one, two or three substituents selected from $C_{1-4}$alkyl, $C_{1-4}$alkoxy, hydroxy, amino, halogen, or trihalo $C_{1-4}$alkyl;

$R_2$ is hydrogen, or $C_{1-4}$alkyl;

or $R_1$ and $R_2$ taken together form an optionally substituted pyrrolidinyl, morpholinyl, piperidinyl or piperazinyl ring, wherein the pyrrolidinyl, morpholinyl, piperidinyl or piperazinyl ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl;

$R_3$ is benzyl substituted with halo; and $R_4$ is hydrogen.

An example of the present invention is a compound of Formula (I) and a form thereof wherein $R_1$ is $C_{1-4}$alkyl, trihalo $C_{1-4}$alkyl, or phenyl substituted with $C_{1-4}$alkoxy;

$R_2$ is hydrogen, or $C_{1-4}$alkyl;

$R_3$ is benzyl substituted with halo; and $R_4$ is hydrogen.

An example of the present invention is a compound of Formula (I) and a form thereof wherein $R_1$ and $R_2$ taken together form an optionally substituted pyrrolidinyl, morpholinyl, piperidinyl or piperazinyl ring, wherein the pyrrolidinyl, morpholinyl, piperidinyl or piperazinyl ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl;

$R_2$ is hydrogen, or $C_{1-4}$alkyl;

$R_3$ is benzyl substituted with halo; and $R_4$ is hydrogen.

An example of the present invention is a compound of Formula (I) and a form thereof wherein $R_1$ and $R_2$ taken together form an optionally substituted pyrrolidinyl, morpholinyl, piperidinyl or piperazinyl ring, wherein the pyrrolidinyl or piperazinyl ring is optionally substituted with one substituent selected from $C_{1-4}$alkyl, $C_{1-4}$alkoxy-$C_{1-4}$alkyl, hydroxy-$C_{1-4}$alkyl;

$R_2$ is hydrogen, or $C_{1-4}$alkyl;

$R_3$ is benzyl substituted with halo; and $R_4$ is hydrogen.

An example of the present invention is a compound of Formula (I) and a form thereof wherein the compound has an E-configuration.

Compounds representative of a compound of Formula (I) or a form thereof, wherein substituents on each side of the iminomethyl double bond in Formula (I) may be in the E or Z configuration, include compounds and forms thereof selected from:

Cpd 1

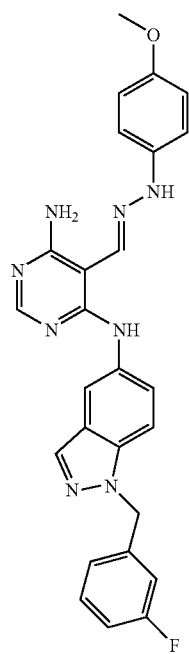

Cpd 2

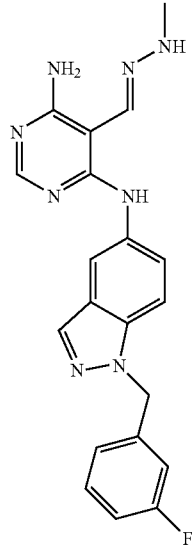

Cpd 3

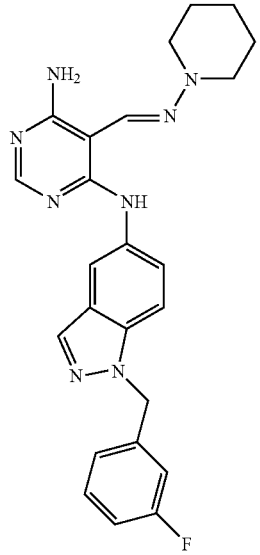

Cpd 4

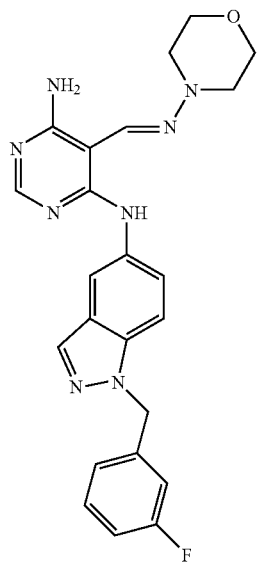

Cpd 5
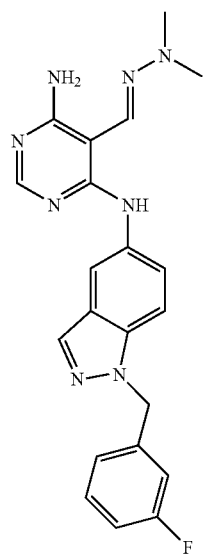
Cpd 6
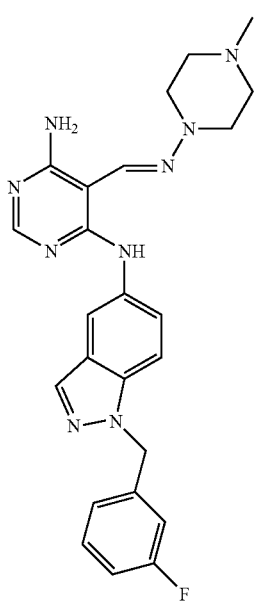
Cpd 7
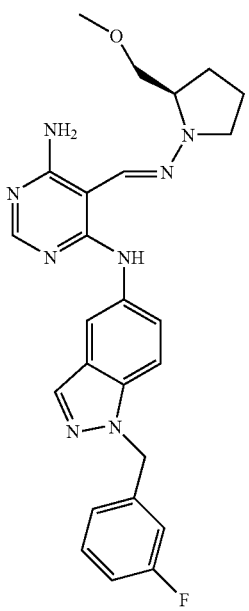
Cpd 8
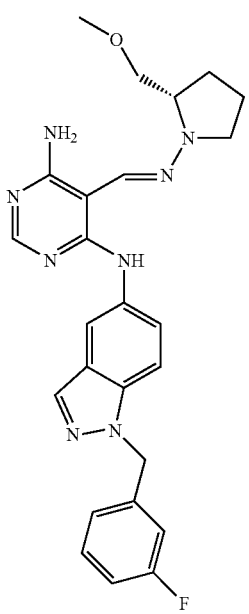

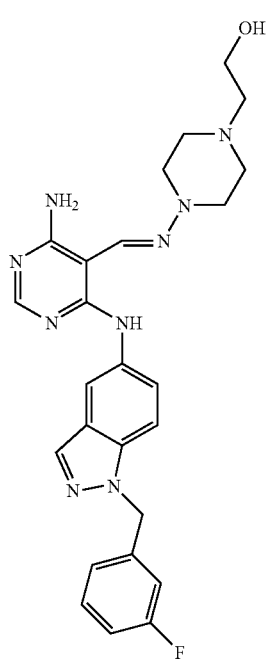

Cpd 9

Cpd 10

Compound Forms

The term "form" means, in reference to compounds of the present invention, such may exist as, without limitation, a salt, stereoisomer, tautomer, crystalline, polymorph, amorphous, solvate, hydrate, ester, prodrug or metabolite form. The present invention encompasses all such compound forms and mixtures thereof.

The term "isolated form" means, in reference to compounds of the present invention, such may exist in an essentially pure state such as, without limitation, an enantiomer, a racemic mixture, a geometric isomer (such as a cis or trans stereoisomer), a mixture of geometric isomers, and the like. The present invention encompasses all such compound forms and mixtures thereof.

The compounds of the invention may be present in the form of pharmaceutically acceptable salts. For use in medicines, the "pharmaceutically acceptable salts" of the compounds of this invention refer to non-toxic acidic/anionic or basic/cationic salt forms.

Suitable salt forms include acid addition salts which may, for example, be formed by mixing a solution of the compound according to the invention with a solution of an acid such as acetic acid, adipic acid, benzoic acid, carbonic acid, citric acid, fumaric acid, glycolic acid, hydrochloric acid, maleic acid, malonic acid, phosphoric acid, saccharinic acid, succinic acid, sulphuric acid, tartaric acid, trifluoroacetic acid and the like.

Furthermore when the compounds of the present invention carry an acidic moiety, suitable salts thereof may include alkali metal salts, e.g. sodium or potassium salts; alkaline earth metal salts, e.g. calcium or magnesium salts; and salts formed with suitable organic ligands, e.g. quaternary ammonium salts.

Thus, representative salts include the following: acetate, adipate, benzenesulfonate, benzoate, bicarbonate, bisulfate, bitartrate, borate, bromide, calcium, camsylate (or camphorsulphonate), carbonate, chloride, clavulanate, citrate, dihydrochloride, edetate, fumarate, gluconate, glutamate, glyconate, hydrabamine, hydrobromine, hydrochloride, iodide, isothionate, lactate, malate, maleate, malonate, mandelate, mesylate, nitrate, oleate, pamoate, palmitate, phosphate/diphosphate, saccharinate, salicylate, stearate, sulfate, succinate, tartrate, tosylate, trichloroacetate, trifluoroacetate and the like.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, $3^{rd}$ Edition, John Wiley & Sons, 1999. The protecting groups may be removed at a convenient subsequent stage using methods known in the art. The scope of the present invention encompasses all such protected compound forms and mixtures thereof.

The invention includes compounds of various isomers and mixtures thereof. The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (optical isomers).

The term "stereoisomer" refers to a isomers that have the same molecular formula and the same sequence of covalently bonded atoms but a different spatial orientation.

The term "optical isomer" means isomers of identical constitution that differ only in the spatial arrangement of their groups. Optical isomers rotate the plane of polarized light in different directions. The term "optical activity" means the degree to which an optical isomer rotates the plane of polarized light.

The term "racemate" or "racemic mixture" means an equimolar mixture of two enantiomeric species, wherein each of the isolated species rotates the plane of polarized light in the opposite direction such that the mixture is devoid of optical activity.

The term "enantiomer" means a stereoisomer that is not nonsuperimposable with its mirror image. The term "diastereomer" means stereoisomers that are not enantiomers.

The term "chiral molecule" means a molecule that has at least one pair of enantiomers. This is in contrast to achiral molecules that can be superimposed on their mirror images.

The two distinct mirror image versions of the chiral molecule are also known as levo (left-handed), abbreviated L, or dextro (right-handed), abbreviated D, depending on which way they rotate polarized light. The symbols "R" and "S" represent the configuration of groups around a stereogenic carbon atom(s).

An example of an enantiomerically enriched form isolated from a racemic mixture includes a dextrorotatory enantiomer, wherein the mixture is substantially free of the levorotatory isomer. In this context, substantially free means the levorotatory isomer may, in a range, comprise less than 25% of the mixture, less than 10%, less than 5%, less than 2% or less than 1% of the mixture according to the formula:

$$\% \text{ levorotatory} = \frac{(\text{mass levorotatory})}{(\text{mass dextrorotatory}) + (\text{mass levorotatory})} \times 100$$

Similarly, an example of an enantiomerically enriched form isolated from a racemic mixture includes a levorotatory enantiomer, wherein the mixture is substantially free of the dextrorotatory isomer. In this context, substantially free means the dextrorotatory isomer may, in a range, comprise less than 25% of the mixture, less than 10%, less than 5%, less than 2% or less than 1% of the mixture according to the formula:

$$\% \text{ dextrorotatory} = \frac{(\text{mass dextrorotatory})}{(\text{mass dextrorotatory}) + (\text{mass levorotatory})} \times 100$$

The term "geometric isomer" means isomers that differ in the orientation of substituent atoms in relationship to a carbon-carbon double bond, to a cycloalkyl ring, or to a bridged bicyclic system. Substituent atoms (other than hydrogen) on each side of a double bond may be in an E or Z configuration. In the "E" configuration, the substituents are on opposite sides in relationship to the double bond. In the "Z" configuration, the substituents are oriented on the same side in relationship to the double bond.

Substituent atoms (other than hydrogen) attached to a ring system may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

The isomeric descriptors ("R," "S," "E," and "Z") indicate atom configurations and are intended to be used as defined in the literature.

The compounds of the invention may be prepared as individual isomers by either isomer-specific synthesis or resolved from an isomeric mixture. Conventional resolution techniques include combining the free base (or free acid) of each isomer of an isomeric pair using an optically active acid (or base) to form an optically active salt (followed by fractional crystallization and regeneration of the free base), forming an ester or amide of each of the isomers of an isomeric pair by reaction with an appropriate chiral auxiliary (followed by fractional crystallization or chromatographic separation and removal of the chiral auxiliary), or separating an isomeric mixture of either an intermediate or a final product using various well known chromatographic methods.

Furthermore, compounds of the present invention may have one or more polymorph or amorphous crystalline forms and, as such, are intended to be included in the scope of the invention. In addition, some of the compounds may form solvates with water (i.e., hydrates) or common organic solvents (e.g., organic esters such as ethanolate and the like) and, as such, are also intended to be encompassed within the scope of this invention.

Chemical Definitions

As used herein, the following terms are intended to have the following meanings (additional definitions are provided where needed throughout the Specification). The definitions herein may specify that a chemical term has an indicated formula. The particular formula provided is not intended to limit the scope of the invention, but is provided as an illustration of the term. The scope of the per se definition of the term is intended to include the plurality of variations expected to be included by one of ordinary skill in the art.

The term "$C_{1-6}$alkyl," whether used alone or as part of a substituent group, means a straight or branched chain hydrocarbon alkyl radical or alkyldiyl linking group, respectively, comprising from 1 to 6 carbon atoms, wherein the radical is derived by the removal of one hydrogen atom from a single carbon atom and the alkyldiyl linking group is derived by the removal of one hydrogen atom from each of two carbon atoms in the chain, such as, for example methyl, ethyl, 1-propyl, 2-propyl, 1-butyl, 2-butyl, tertiary butyl, 1-pentyl, 2-pentyl, 3-pentyl, 1-hexyl, 2-hexyl, 3-hexyl and the like. Examples include $C_{1-4}$alkyl groups. $C_{1-6}$alkyl is substituted on one or more available carbon chain atoms with one or more substituents when allowed by available valences.

The term "$C_{1-6}$alkoxy" means an alkyl radical or linking group having from 1-6 carbon atoms in a linear or branched arrangement, wherein the radical or linking group is attached through an oxygen linking atom, as in the formula: —O—$C_{1-6}$alkyl. The term "$C_{1-6}$alkoxy" also includes a "$C_{1-4}$ alkoxy" radical or linking group having from 1 up to 4 carbon atoms respectively, such as methoxy, ethoxy, propoxy, butoxy and the like. An alkoxy radical or linking group may be attached to a core molecule and further substituted as a linking group where indicated.

The term "$C_{1-6}$alkoxy-$C_{1-6}$alkyl" means a radical of the formula:

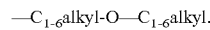

—$C_{1-6}$alkyl-O—$C_{1-6}$alkyl.

The term "amino" means a radical of the formula: —$NH_2$.

The term "$C_{3-6}$cycloalkyl" means a saturated or partially unsaturated, monocyclic or polycyclic hydrocarbon ring system radical derived by the removal of one hydrogen atom from a single ring carbon atom. Typical cycloalkyl radicals include cyclopropyl, cyclobutyl, cyclopentyl or cyclohexyl. $C_{3-6}$cycloalkyl is substituted on one or more available ring carbon atoms with one or more substituents when allowed by available valences.

The term "benzyl" means a radical of the formula: —$CH_2$-phenyl, wherein phenyl is optionally further substituted.

The term "hetero," when used as a prefix for a ring system, refers to the replacement of at least one carbon atom member in the ring system with a heteroatom selected from N, O, S, S(O), or $SO_2$. A hetero ring may have 1, 2, 3, or 4 carbon atom members replaced by a nitrogen atom. Alternatively, a ring may have 0, 1, 2, or 3 nitrogen atom members and 1 oxygen or sulfur atom member. Alternatively, up to two adjacent ring members may be heteroatoms, wherein one heteroatom is nitrogen and the other heteroatom is selected from N, S, or O.

The term "heterocyclyl" means a saturated or partially unsaturated monocyclic or polycyclic "hetero" ring system radical having a cycloalkyl ring as the core molecule. Heterocyclyl ring systems include 2H-pyrrole, 2-pyrrolinyl, 3-pyrrolinyl, pyrrolidinyl, 1,3-dioxolanyl, 2-imidazolinyl (also referred to as 4,5-dihydro-1H-imidazolyl), imidazolidinyl, 2-pyrazolinyl, pyrazolidinyl, tetrazolyl, tetrazolidinyl, piperidinyl, 1,4-dioxanyl, morpholinyl, 1,4-dithianyl, thiomorpholinyl, piperazinyl, azetidinyl, azepanyl, hexahydro-1,4-diazepinyl, hexahydro-1,4-oxazepanyl, tetrahydro-furanyl, tetrahydro-thienyl, tetrahydro-pyranyl, tetrahydro-pyridazinyl and the like. The term "heterocyclyl" also includes a benzofused-heterocyclyl ring system radical and the like, such as indolinyl (also referred to as 2,3-dihydro-indolyl), benzo[1,3]dioxolyl (also referred to as 1,3-benzodioxolyl), 2,3-dihydro-1,4-benzodioxinyl, 2,3-dihydro-benzofuranyl, 1,2-dihydro-phthalazinyl and the like. Heterocyclyl radicals may be attached to a core molecule and further substituted on any atom when allowed by available valences.

The term "halogen" or "halo" means the group chloro, bromo, fluoro or iodo.

The term "hydroxy-$C_{1-6}$alkyl" means a radical of the formula: —$C_{1-6}$alkyl-hydroxy, wherein $C_{1-6}$alkyl is substituted on one or more available carbon chain atoms with one or more hydroxy radicals when allowed by available valences.

The term "iminomethyl" means a radical of the formula: —CH=N—, wherein substituents on each side of the iminomethyl double bond may be in the E or Z configuration.

The term "trihalo-$C_{1-6}$alkyl" means a radical of the formula: —$C_{1-6}$alkyl-trihalo, wherein $C_{1-6}$alkyl is substituted on a terminal carbon chain atom with three halogen atoms.

The term "substituted," refers to a core molecule on which one or more hydrogen atoms have been replaced with one or more functional radical moieties. The number that is allowed by available valences limits the amount of substituents. Substitution is not limited to the core molecule, but may also occur on a substituent radical, whereby the substituent radical becomes a linking group.

Therapeutic Use

The compounds of Formula (I) or a form thereof are useful as inhibitors of ATP-protein kinase interactions.

The present invention includes the use of one or more compounds of Formula (I) or a form thereof as protein kinase inhibitors, wherein the protein kinases include serine/threonine kinases and tyrosine kinases.

Examples of the present invention include protein kinases selected from EGFR and HER2, wherein the compounds of Formula (I) or a form thereof are useful for preventing, treating or ameliorating chronic or acute kinase mediated diseases.

Embodiments of kinase-mediated diseases include an EGFR protein kinase mediated CMV infection. In a related embodiment, the compounds of Formula (I) or a form thereof are useful contraceptive agents.

The present invention is further directed to a method for ameliorating, treating or preventing a chronic or acute kinase mediated disease in a patient in need thereof comprising administering to the patient an effective amount of one or more compounds of Formula (I) or a form thereof.

Embodiments of the present invention include a chronic or acute disease mediated by a kinase selected from EGFR and HER2.

An aspect of the method includes inhibiting unregulated kinase activity in the patient, as well as unregulated kinase expression or signaling, unregulated expression or signaling of a kinase selected from EGFR and HER2 and unregulated expression or signaling which results in unregulated cell proliferation. Such unregulated cell proliferation includes cancer, metastatic cancer cell invasion or metastatic cancer cell migration. Cancer further includes tumors mediated by the unregulated activity of kinases selected from EGFR and HER2, including non-small-cell lung cancers, colon cancers, breast cancers and the like. An aspect of the method also includes an amount of one or more compounds of Formula (I) or a form thereof, which is effective to induce remission of a chronic form of a cancer. Such an amount includes an amount that is effective at a low dose to inhibit unregulated kinase activity.

The present invention includes the use of one or more compounds of Formula (I) or a form thereof in the preparation of a composition or medicament for preventing, treating or ameliorating chronic or acute kinase mediated diseases.

The term "chronic or acute kinase mediated disease" as used herein, includes, and is not limited to diseases, disorders, syndromes or conditions associated with unregulated kinase activity and diseases, disorders, syndromes or conditions that accompany such activity.

The term "unregulated kinase activity" refers to 1) increased or unregulated kinase expression or signaling, 2) increased kinase expression leading to unregulated cell proliferation, 3) increased kinase signaling leading to unregulated cell proliferation, or 4) mutations leading to constitutive kinase activation. The existence of unregulated kinase activity may be determined by procedures well known in the art.

The term "unregulated cell proliferation" refers to cell proliferation of one or more subset of cells in a multicellular organism resulting in harm (such as discomfort or decreased life expectancy) to the multicellular organism.

Tumor cells that result from unregulated cell proliferation use many mechanisms to enhance their survival and spread and often have high rates of proliferation because growth control signals that keep normal cells in check are defective. Many tumor cells secrete autocrine growth factors that increase proliferation rates or they induce other cells to secrete growth factors that they utilize.

Tumor cells grow and spread by dislodging from a primary tumor site, using proteases to digest the extracellular matrix, spreading in response to migration cues, allowing them to migrate to certain tissues preferentially where overexpressed adhesion molecules allow attachment and growth at the new site. The totality of these and other biological processes are responsible for the lethal effects of a tumor. A kinase inhibitor may affect one or more aspects of tumor survival mechanisms and thus be therapeutically useful. Alternatively, a kinase inhibitor may not affect one particular tumor survival mechanism but may still be therapeutically useful by affecting tumor survival by an unknown or as yet unelucidated mechanism of action.

The foregoing methods contemplate that a compound of formula (I) or a form thereof is useful for treating diseases, disorders or conditions such as, without limitation, osteoarthritis, rheumatoid arthritis, synovial pannus invasion in arthritis, multiple sclerosis, myasthenia gravis, diabetes mellitus, diabetic angiopathy, diabetic retinopathy, retinal vessel proliferation, inflammatory bowel disease, Crohn's disease, ulcerative colitis, bone diseases, transplant or bone marrow transplant rejection, lupus, chronic pancreatitis, cachexia, septic shock, fibroproliferative and differentiative skin diseases or disorders, central nervous system diseases, neurodegenerative diseases, disorders or conditions related to nerve damage and axon degeneration subsequent to a brain or spinal cord injury, acute or chronic cancer, ocular diseases, viral infections, heart disease, lung or pulmonary diseases or kidney or renal diseases.

Certain diseases, disorders or conditions further include, without limitation, acute or chronic cancer selected from bladder cancer, brain, head or neck cancer, breast cancer, colorectal cancer, endometrial cancer, epidermoid cancer, esophageal cancer, gastric cancer, glioma cancer, lung cancer, ovarian cancer, pancreatic cancer, prostate cancer, renal cell cancer, Kaposi's sarcoma, leukemia, lymphoma or papillocarcinoma; and, cancer-associated pathologies selected from abnormal cell proliferation, unregulated cell proliferation, tumor growth, tumor angiopathy, tumor angiogenesis, tumor vascularization or metastatic cancer cell invasion and migration.

Certain diseases, disorders or conditions further include, without limitation, fibroproliferative and differentiative skin diseases or disorders selected from papilloma formation, psoriasis, dermatitis, eczema, seborrhea or chemotherapy-induced alopecia; central nervous system diseases selected from Alzheimer's disease, Parkinson's disease or depression; ocular diseases selected from macular degeneration, diseases of the cornea or glaucoma; viral infections selected from mycotic infection, autoimmune disease or cytomegalovirus; heart disease selected from atherosclerosis, neointima formation or transplantation-induced vasculopathies such as arterial restenosis; lung or pulmonary diseases selected from allergic-asthma, lung fibrosis, pulmonary fibrosis or chronic obstructive pulmonary disorder; and, kidney or renal diseases selected from acute, subacute or chronic forms of glomerulonephritis or membranoproliferative glomerulonephritis, glomerulosclerosis, congenital multicystic renal dysplasia or kidney fibrosis.

Certain HER2 kinase mediated cancer includes, without limitation, bladder cancer, brain, head or neck cancer, breast cancer, colorectal cancer, gastric cancer, endometrial cancer, esophageal cancer, lung cancer, ovarian cancer, prostate cancer or renal cell cancer.

The term "myasthenia gravis" means a disease having the characteristic feature of easy fatigue of certain voluntary muscle groups on repeated use. Muscles of the face or upper trunk are especially likely to be affected. In most and perhaps all cases, the disease is due to the development of autoantibodies against the acetylcholine receptor in neuromuscular junctions. Immunization of animals with this receptor protein leads to a disease with the features of myasthenia gravis.

In reference to "synovial pannus invasion in arthritis," the term "pannus" means a disease whereby vascularised granulation tissue rich in fibroblasts, lymphocytes and macrophages, derived from synovial tissue, overgrows the bearing surface of the joint in rheumatoid arthritis and is associated with the breakdown of the articular surface.

The term "administering" with respect to the methods of the present invention, refers to a means for treating, ameliorating or preventing a disease as described herein with a compound specifically disclosed or a compound or prodrug thereof, which would obviously be included within the scope of the invention albeit not specifically disclosed for certain of the instant compounds.

Such methods include administering an effective amount of one or more compounds of Formula (I) or a form, composition or medicament thereof at different times during the course of a therapy or concurrently in a combination form. Such methods further include administering an effective amount of one or more compounds of Formula (I) or a form, composition or medicament thereof with one or more agents at different times during the course of a therapy or concurrently in a combination form.

The term "prodrug" refers to a metabolic precursor of a compound of Formula (I) or a form thereof. In general, a prodrug is a functional derivative of a compound that may be inactive when administered to a patient but is readily convertible in vivo into an active metabolite compound.

The term "active metabolite" refers to a metabolic product of a compound that is effective for preventing, treating or ameliorating a chronic or acute kinase mediated disease. Conventional procedures for the selection and preparation of suitable prodrug derivatives are described, for example, in "Design of Prodrugs", ed. H. Bundgaard, Elsevier, 1985.

The term "patient" as used herein, refers to an animal, preferably a mammal, and most preferably a human, who has been the object of treatment, observation or experiment and is at risk of (or susceptible to) developing a disease or having a disease related to unregulated kinase activity.

The term "effective amount" refers to that amount of active compound or pharmaceutical agent that elicits the biological or medicinal response (such as inhibiting unregulated kinase activity) in a patient's tissue system, animal or human, that is being sought by a researcher, veterinarian, medical doctor, or other clinician, which includes preventing, treating or ameliorating the symptoms of the chronic or acute kinase mediated disease being treated.

The effective amount of a compound of Formula (I) exemplified in such a method is from about 0.001 mg/kg/day to about 300 mg/kg/day or has an $IC_{50}$ (50% inhibition concentration) of about 25 μM or less, or about 10 μM or less, preferably of about 1 μM or less, more preferably of about 0.5 μM or less, and most preferably of about 0.1 μM or less.

The term "composition" refers to a product containing one or more compounds of Formula (I) or a form thereof (such as a product comprising the specified ingredients in the specified amounts, as well as any product which results, directly or indirectly, from such combinations of the specified ingredients in the specified amounts).

The term "medicament" refers to one or more compounds of Formula (I) or a form thereof used in a product for use in preventing, treating or ameliorating a chronic or acute kinase mediated disease.

A formulation of a composition or medicament of the present invention is "pharmaceutically acceptable" when the molecular entities and components used therein are of sufficient purity and quality such that, when appropriately administered to an animal or a human, the formulation does not produce an adverse, allergic or other untoward reaction. Since both human use (clinical and over-the-counter) and veterinary use are equally included within the scope of the present invention, a pharmaceutically acceptable formulation would include a composition or medicament for either human or veterinary use.

The term "combination therapy" refers to the use of one or more compounds of Formula (I) or a form, composition or medicament thereof in combination with one or more therapeutic agents for preventing, treating or ameliorating a chronic or acute kinase mediated disease and advantageously may facilitate the use of a reduced effective dose of the compound of Formula (I) and/or the therapeutic agent than would be recommended for the treatment of a particular unregulated cell proliferation disorder. Therefore, it is contemplated that the compounds of this invention can be used before, during or after treatment with a particular therapeutic agent.

The term "therapeutic agent" refers to chemotherapeutic agents used to treat a kinase mediated cancer or antiviral agents used to treat cytomegalovirus. Chemotherapeutic agents include and are not limited to anti-angiogenic agents, anti-tumor agents, cytotoxic agents, inhibitors of cell proliferation, radiation therapy and the like or mixtures thereof.

The term "preventing, treating or ameliorating" refers, without limitation, to facilitating the eradication of, inhibiting the progression of or promoting stasis of a malignancy.

The term "radiation therapy" refers to a therapy that comprises exposing the patient in need thereof to radiation. The present invention includes a method for administering one or more compounds of Formula (I) or a form, composition or medicament thereof in combination with radiation therapy. Procedures for administering such therapy are known to those skilled in the art. The appropriate scheme of radiation therapy will be similar to those already employed in clinical therapies wherein the radiation therapy is used alone or in combination with other chemotherapeutic agents.

Pharmaceutical Compositions

An embodiment of the present invention includes a composition comprising an admixture of one or more compounds of Formula (I) and/or one or more forms thereof and one or more excipients.

The forms for a compound of Formula (I) include a salt, ester, prodrug or active metabolite of a compound of Formula (I). The form for a compound of Formula (I) further includes a radiolabeled compound of Formula (I), whereby at least one hydrogen atom of the compound of Formula (I) is replaced with a deuterium or tritium atom. Other labeling techniques known to those skilled in the arts may also be used.

The present invention further includes the use of a process for making the composition or medicament comprising mixing one or more of the instant compounds and an optional carrier; and, includes those compositions or medicaments resulting from such a process. Contemplated processes include both conventional and unconventional pharmaceutical techniques.

The composition or medicament may take a wide variety of forms to effectuate mode of administration, including, but not limited to, intravenous (both bolus and infusion), oral, nasal, transdermal, topical with or without occlusion, and injection intraperitoneally, subcutaneously, intramuscularly, intratumorally or parenterally. The composition or medicament may be in a dosage unit such as a tablet, pill, capsule, powder, granule, sterile parenteral solution or suspension, metered aerosol or liquid spray, drop, ampoule, auto-injector device or suppository; for administration orally, parenterally, intranasally, sublingually or rectally or by inhalation or insufflation.

Compositions or medicaments suitable for oral administration include solid forms such as pills, tablets, caplets, capsules (each including immediate release, timed release and sustained release formulations), granules and powders; and, liquid forms such as solutions, syrups, elixirs, emulsions and suspensions. Forms useful for parenteral administration include sterile solutions, emulsions and suspensions. Alternatively, the composition or medicament may be presented in a form suitable for once-weekly or once-monthly administration; for example, an insoluble salt of the active compound, such as the decanoate salt, may be adapted to provide a depot preparation for intramuscular injection.

The dosage form (tablet, capsule, powder, injection, suppository, teaspoonful and the like) containing one or more compounds of Formula (I) or a form, composition or medicament thereof as an active ingredient contains an effective amount of the active ingredient necessary to be therapeutically or prophylactically effective.

The composition or medicament may contain from about 0.001 mg to about 5000 mg (preferably, from about 0.001 to about 500 mg) of active ingredient and may be constituted into any form suitable for the mode of administration selected for a patient in need. A contemplated effective amount may range from about 0.001 mg to about 300 mg/kg of body weight per day. A contemplated effective amount may also range from about 0.003 to about 100 mg/kg of body weight per day. Another contemplated effective amount may range from about 0.1 to about 100 mg/kg of body weight per day. Another contemplated effective amount may also range from about 0.005 to about 15 mg/kg of body weight per day. The composition or medicament may be administered according to a dosage regimen of from about 1 to about 5 times per day.

For oral administration, the composition or medicament is preferably in the form of a tablet containing, e.g., 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. Optimal dosages will vary depending on factors associated with the particular patient being treated (e.g., age, weight, diet and time of administration), the severity of the condition being treated, the compound being employed, the mode of administration and the strength of the preparation. The use of either daily administration or post-periodic dosing may be employed.

A radiolabeled form of a compound of Formula (I), whereby at least one hydrogen atom of the compound of Formula (I) is replaced with a labeling atom such as a deuterium or tritium atom, may be used as a marker for the kinase receptor. Other labeling techniques known to those skilled in the arts may also be used.

Examples of the present invention further include methods for using a compound of Formula (I) or a form thereof in a pharmaceutical composition or medicament as described herein selected from the group consisting of:

| Cpd | Name |
|---|---|
| 1 | N-[1-(3-fluoro-benzyl)-1H-indazol-5-yl]-5-[(4-methoxy-phenyl)-hydrazonomethyl]-pyrimidine-4,6-diamine, |
| 2 | N-[1-(3-fluoro-benzyl)-1H-indazol-5-yl]-5-(methyl-hydrazonomethyl)-pyrimidine-4,6-diamine, |
| 3 | N-[1-(3-fluoro-benzyl)-1H-indazol-5-yl]-5-(piperidin-1-yliminomethyl)-pyrimidine-4,6-diamine, |
| 4 | N-[1-(3-fluoro-benzyl)-1H-indazol-5-yl]-5-(morpholin-4-yliminomethyl)-pyrimidine-4,6-diamine, |
| 5 | 5-(dimethyl-hydrazonomethyl)-N-[1-(3-fluoro-benzyl)-1H-indazol-5-yl]-pyrimidine-4,6-diamine, |
| 6 | N-[1-(3-fluoro-benzyl)-1H-indazol-5-yl]-5-[(4-methyl-piperazin-1-ylimino)-methyl]-pyrimidine-4,6-diamine, |
| 7 | N-[1-(3-fluoro-benzyl)-1H-indazol-5-yl]-5-{[(2R)-2-methoxymethyl-pyrrolidin-1-ylimino]-methyl}-pyrimidine-4,6-diamine, |
| 8 | N-[1-(3-fluoro-benzyl)-1H-indazol-5-yl]-5-{[(2S)-2-methoxymethyl-pyrrolidin-1-ylimino]-methyl}-pyrimidine-4,6-diamine, |
| 9 | 2-[4-({4-amino-6-[1-(3-fluoro-benzyl)-1H-indazol-5-ylamino]-pyrimidin-5-ylmethylene}-amino)-piperazin-1-yl]-ethanol, and |
| 10 | N-[1-(3-fluoro-benzyl)-1H-indazol-5-yl]-5-[(2,2,2-trifluoro-ethyl)-hydrazonomethyl]-pyrimidine-4,6-diamine. |

Examples of the present invention further include methods for using a compound of Formula (I) or a form thereof in a pharmaceutical composition or medicament as described herein selected from the group consisting of:

| Cpd | Name |
|---|---|
| 4 | N-[1-(3-fluoro-benzyl)-1H-indazol-5-yl]-5-(morpholin-4-yliminomethyl)-pyrimidine-4,6-diamine, |
| 5 | 5-(dimethyl-hydrazonomethyl)-N-[1-(3-fluoro-benzyl)-1H-indazol-5-yl]-pyrimidine-4,6-diamine, |
| 6 | N-[1-(3-fluoro-benzyl)-1H-indazol-5-yl]-5-[(4-methyl-piperazin-1-ylimino)-methyl]-pyrimidine-4,6-diamine, and |
| 9 | 2-[4-({4-amino-6-[1-(3-fluoro-benzyl)-1H-indazol-5-ylamino]-pyrimidin-5-ylmethylene}-amino)-piperazin-1-yl]-ethanol. |

Synthetic Methods

Representative compounds of the present invention can be synthesized in accordance with the general synthetic schemes described below and are illustrated more particularly in the specific synthetic examples that follow. The general schemes and specific examples are offered by way of illustration; the invention should not be construed as being limited by the chemical reactions and conditions expressed. The methods for preparing the various starting materials used in the schemes and examples are well within the skill of persons versed in the art. No attempt has been made to optimize the yields obtained in any of the example reactions. One skilled in the art would know how to increase such yields through routine variations in reaction times, temperatures, solvents and/or reagents.

The terms used in describing the invention are commonly used and known to those skilled in the art. When used herein, the following abbreviations or formulas have the indicated meanings:

| Abbreviation | Meaning |
|---|---|
| Cpd | compound |
| DIEA | diisopropylethylamine |
| DMSO | dimethyl sulfoxide |
| EtOAc | ethyl acetatate |
| i-PrOH | isopropanol |
| min/h/hr | minute/hour |
| RT/R.T./rt/r.t. | room temperature |
| TFA | trifluoroacetic acid |

General Synthetic Methods

Representative compounds of the present invention can be synthesized in accordance with the general synthetic methods described below and are illustrated more particularly in the schemes that follow. Since the schemes are illustrations, the invention should not be construed as being limited by the chemical reactions and conditions expressed. The preparation of the various starting materials used in the schemes is well within the skill of persons versed in the art.

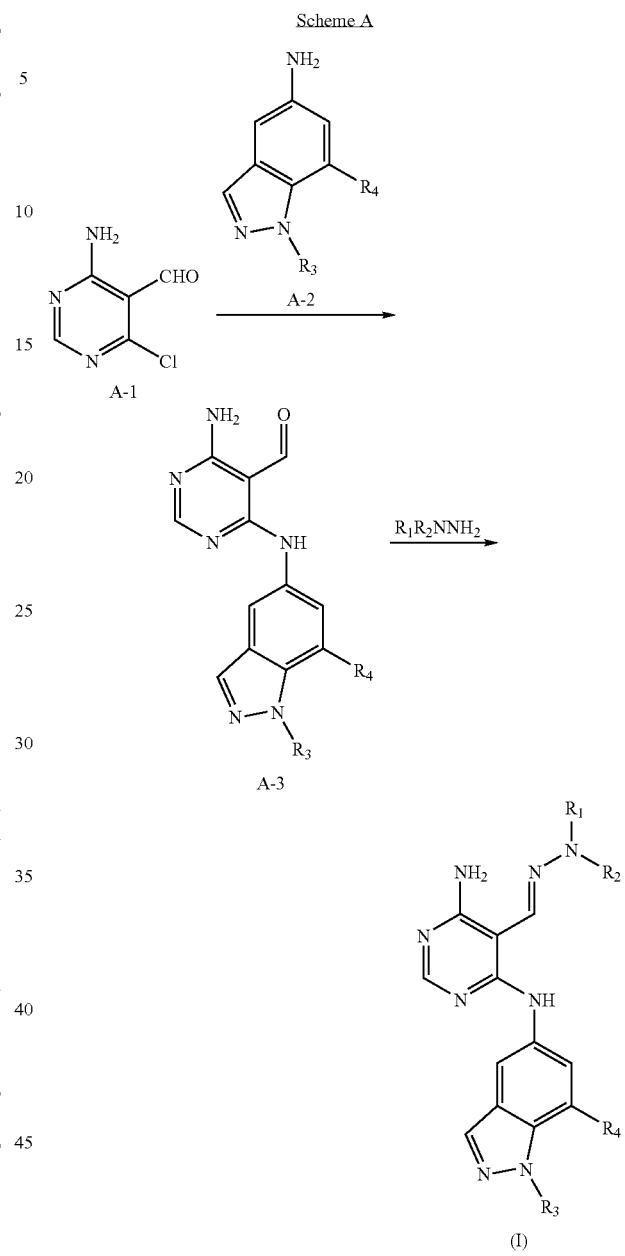

Scheme A

In accordance with Scheme A, a commercially available pyrimidine Compound A1 in a solvent, such as DMSO and the like is reacted with Compound A2 to provide an intermediate aldehyde Compound A3.

Compound A3, in a solvent such as isopropanol and the like, is reacted with a hydrazine derivative $R_1R_2NNH$ to provide a Compound of Formula (I) (and a form thereof, wherein substituents on each side of the iminomethyl double bond in Formula (I) may be in the E or Z configuration).

SPECIFIC SYNTHETIC EXAMPLES

Specific compounds which are representative of this invention were prepared as per the following examples and reaction sequences; the examples and the diagrams depicting the reaction sequences are offered by way of illustration, to aid in the understanding of the invention and should not be construed to limit in any way the invention set forth in the claims which follow thereafter. The depicted intermediates may also be used in subsequent examples to produce additional compounds of the present invention. No attempt has been made to optimize the yields obtained in any of the reactions. One skilled in the art would know how to increase such yields through routine variations in reaction times, temperatures, solvents and/or reagents.

Example 1

5-(dimethyl-hydrazonomethyl)-N-[1-(3-fluoro-benzyl)-1H-indazol-5-yl]-pyrimidine-4,6-diamine (Compound 5)

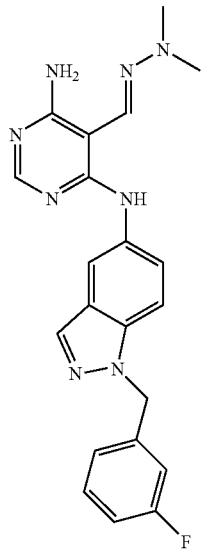

A. Preparation of 4-amino-6-[1-(3-fluoro-benzyl)-1H-indazol-5-ylamino]-pyrimidine-5-carbaldehyde To a mixture of 4-amino-6-chloro-pyrimidine-5-carbaldehyde (95.5 mg, 0.61 mmol) and 1-(3-fluoro-benzyl)-1H-indazol-5-ylamine (147 mg, 0.61 mmol) in DMSO (1.5 mL) was added diisopropylethylamine (DIEA, 79 mg, 0.61 mmol). The mixture was stirred at 100° C. for 2 h, cooled to room temperature, then partitioned between ethyl acetate and $H_2O$. The combined ethyl acetate extracts were dried over $Na_2SO_4$ and evaporated to afford a yellow solid, which was used in the next step without further purification.

A. Preparation of 5-(dimethyl-hydrazonomethyl)-N-[1-(3-fluoro-benzyl)-1H-indazol-5-yl]-pyrimidine-4,6-diamine A mixture of crude 4-amino-6-[1-(3-fluoro-benzyl)-1H-indazol-5-ylamino]-pyrimidine-5-carbaldehyde (14.2 mg, 0.039 mmol) and methylhydrazine (5.4 mg, 0.118 mmol) in i-PrOH (1.5 mL) was stirred at 95° C. for 3 h, then diluted with water. The yellow precipitate was extracted with ethyl acetate (35 mL) and the organic extracts were evaporated. The residue was purified by flash column chromatography on silica gel (EtOAc then to 5% MeOH/EtOAc) to give the desired product (14.3 mg, 94%).

$^1$H NMR (CD$_3$OD) δ 8.04 (d, J=0.91 Hz, 1H), 7.98 (dd, J=1.92 and 0.77 Hz, 1H), 7.87 (s, 1H), 7.63 (s, 1H), 7.50 (dt, J=8.98 and 0.82 Hz, 1H), 7.42 (dd, J=8.93 and 1.90 Hz, 1H), 7.30 (td, J=8.15 and 5.86 Hz, 1H), 6.94-7.03 (2H), 6.87 (m, 1H), 5.65 (s, 2H), 2.96 (s, 6H). LC-MS R$_t$=1.21 min, m/z 405.2 (MH$^+$).

Using the procedure of Example 1 or other conventional methods known to those skilled in the art, other compounds representative of the present invention were prepared:

| Cpd | Name/Data |
|---|---|
| 1 | N-[1-(3-fluoro-benzyl)-1H-indazol-5-yl]-5-[(4-methoxy-phenyl)-hydrazonomethyl]-pyrimidine-4,6-diamine $^1$H NMR (CDCl$_3$) δ 8.08 (s, 1H), 8.00 (s, 1H), 7.93 (2H), 7.36 (1H), 7.17-7.26 (2H), 6.78-6.96 (7H), 5.51 (s, 2H), 3.73 (s, 3H). LC-MS R$_t$ = 1.65 min, m/z 483.2 (MH$^+$). |
| 2 | N-[1-(3-fluoro-benzyl)-1H-indazol-5-yl]-5-(methyl-hydrazonomethyl)-pyrimidine-4,6-diamine $^1$H NMR (CDCl$_3$) δ 10.19 (br, 1H), 8.13 (s, 1H), 8.01 (s, 1H), 7.97 (s, 1H), 7.69 (1H), 7.43 (dd, J = 8.80 and 1.85 Hz, 1H), 7.21-7.29 (3H), 6.95 (3H), 6.91 (1H), 6.84 (m, 1H), 5.57 (s, 2H), 3.00 (s, 3H). LC-MS R$_t$ = 1.08 min, m/z 391.0 (MH$^+$). |
| 3 | N-[1-(3-fluoro-benzyl)-1H-indazol-5-yl]-5-(piperidin-1-yliminomethyl)-pyrimidine-4,6-diamine $^1$H NMR (CDCl$_3$) δ 10.93 (br, 1H), 8.12 (s, 1H), 8.02 (d, J = 0.84 Hz, 1H), 8.01 (d, J = 1.83 Hz, 1H), 7.73 (s, 1H), 7.43 (dd, J = 8.91 and 1.98 Hz, 1H), 7.22-7.34 (2H), 6.91-6.97 (2H), 6.84 (m, 1H), 5.57 (s, 2H), 5.54 (br, 2H), 3.17 (t, J = 5.56 Hz, 4H), 1.78 (m, 4H), 1.57 (m, 2H). LC-MS R$_t$ = 1.46 min, m/z 445.3 (MH$^+$). |
| 4 | N-[1-(3-fluoro-benzyl)-1H-indazol-5-yl]-5-(morpholin-4-yliminomethyl)-pyrimidine-4,6-diamine $^1$H NMR (CDCl$_3$) δ 11.12 (br, 1H), 8.08 (s, 1H), 8.03 (d, J = 0.84 Hz, 1H), 7.96 (d, J = 1.75 Hz, 1H), 7.90 (s, 1H), 7.40 (dd, J = 8.99 and 1.97 Hz, 1H), 7.23-7.32 (2H), 6.91-6.98 (2H), 6.84 (m, 1H), 6.37 (br, 2H), 5.58 (s, 2H), 3.91 (t, J = 4.79 Hz, 4H), 3.23 (t, J = 4.90 Hz, 4H). LC-MS R$_t$ = 1.27 min, m/z 447.3 (MH$^+$). |
| 6 | N-[1-(3-fluoro-benzyl)-1H-indazol-5-yl]-5-[(4-methyl-piperazin-1-ylimino)-methyl]-pyrimidine-4,6-diamine $^1$H NMR (CD$_3$OD) δ 8.04 (d, J = 0.60 Hz, 1H), 8.01 (s, 1H), 7.98 (dd, J = 2.1 and 0.60 Hz, 1H), 7.89 (s, 1H), 7.50 (dd, J = 9.0 and 0.90 Hz, 1H), 7.42 (dd, J = 8.7 and 1.95 Hz, 1H), 7.30 (td, J = 8.10 and 6.0 Hz, 1H), 6.99 (m, 2H), 6.87 (m, 1H), 5.65 (s, 2H), 3.23 (t, J = 4.80 Hz, 4H), 2.67 (t, J = 4.95 Hz, 4H). LC-MS R$_t$ = 0.55 min, m/z 460.2 (MH$^+$). |
| 7 | N-[1-(3-fluoro-benzyl)-1H-indazol-5-yl]-5-{[(2R)-2-methoxymethyl-pyrrolidin-1-ylimino]-methyl}-pyrimidine-4,6-diamine $^1$H NMR (CDCl$_3$) δ 10.43 (s, 1H), 8.12 (s, 1H), 8.01 (d, J = 0.95 Hz, 1H), 8.00 (d, J = 1.66 Hz, 1H), 7.48 (dd, J = 8.91 and 1.99 Hz, 1H), 7.35 (s, 1H), 7.22-7.29 (2H), 6.95 (m, 2H), 6.85 (m, 1H), 5.57 (s, 1H), 5.25 (br, 2H), 3.71 (m, 1H), 3.49-3.58 (3H), 3.30 (s, 3H), 3.05 (m, 1H), 1.97-2.10 (3H), 1.80 (m, 1H). LC-MS R$_t$ = 1.35 min, m/z 475.2 (MH$^+$). |
| 8 | N-[1-(3-fluoro-benzyl)-1H-indazol-5-yl]-5-{[(2S)-2-methoxymethyl-pyrrolidin-1-ylimino]-methyl}-pyrimidine-4,6-diamine $^1$H NMR (CDCl$_3$) δ 10.44 (s, 1H), 8.11 (s, 1H), 8.01 (d, J = 0.79 Hz, 1H), 8.00 (d, J = 1.93 Hz, 1H), 7.48 (dd, J = 8.88 and 1.92 Hz, 1H), 7.35 (s, 1H), 7.22-7.30 (2H), 6.96 (dd, J = 8.08 and 2.08 Hz, 1H), 6.93 (m, 1H), 6.85 (dt, J = 9.56 and 2.10 Hz, 1H), 5.57 (s, 2H), 5.27 (br, 2H), 3.72 (m, 1H), 3.50-3.58 (3H), 3.30 (s, 3H), 3.06 (m, 1H), 1.98-2.10 (3H), 1.79 (m, 1H). LC-MS R$_t$ = 1.36 min, m/z 475.2 (MH$^+$). |

-continued

| Cpd | Name/Data |
|---|---|
| 9 | 2-[4-({4-amino-6-[1-(3-fluoro-benzyl)-1H-indazol-5-ylamino]-pyrimidin-5-ylmethylene}-amino)-piperazin-1-yl]-ethanol<br>$^1$H NMR (DMSO-d$_6$) δ 11.04 (s, 1H), 8.19 (m, 1H), 8.07 (d, J = 0.90 Hz, 1H), 7.97 (d, J = 2.06 Hz, 1H), 7.96 (s, 1H), 7.61 (d, J = 8.88 Hz, 1H), 7.40 (dd, J = 8.95 and 1.92 Hz, 1H), 7.33 (dd, J = 8.08 and 6.20 Hz, 1H), 7.09 (m, 1H), 7.01 (m, 2H), 6.97 (br, 2H), 5.66 (s, 2H), 4.45 (t, J = 5.37 Hz, 1H), 3.52 (dt, J = 5.46 and 6.20 Hz, 2H), 3.16 (t, J = 4.62 Hz, 4H), 2.63 (t, J = 4.71 Hz, 4H), 2.45 (t, J = 6.21 Hz, 2H). LC-MS R$_t$ = 0.80 min, m/z 490.2 (MH$^-$). |
| 10 | N-[1-(3-fluoro-benzyl)-1H-indazol-5-yl]-5-[(2,2,2-trifluoro-ethyl)-hydrazonomethyl]-pyrimidine-4,6-diamine<br>$^1$H NMR (CDCl$_3$) δ 10.22 (br, 1H), 8.13 (s, 1H), 8.09 (s, 1H), 8.03 (d, J = 0.89 Hz, 1H), 7.93 (d, J = 1.58 Hz, 1H), 7.37 (dd, J = 8.93 and 1.94 Hz, 1H), 7.23-7.31 (2H), 6.91-6.98 (2H), 6.84 (m, 1H), 5.88 (br, 2H), 5.57 (s, 2H), 3.83 (m, 2H). LC-MS R$_t$ = 1.35 min, m/z 459.3 (MH$^+$). |

BIOLOGICAL EXAMPLES

The ability of the compounds to treat or ameliorate protein kinase mediated disorders was determined using the following procedures.

Example 1

EGFR Kinase Assay

The EGFR kinase used was a fusion of Glutathione-S-Transferase (GST) and a PCR amplified intracellular portion of EGFR (NM_005228). The intracellular portion of EGFR started at nucleotide 2189 (corresponding to amino acid 667) and ended at the termination codon. The portion was PCR amplified with primers that added the lambda attB sequences to each end, recombined into an entry vector, then into a GST destination vector (as described in Gateway Technologies Manual by Invitrogen Corporation, Carlsbad, Calif.).

The destination vector was recombined in the DH10BAC strain of bacteria to produce a bacmid. The bacmid was transfected into Sf9 cells and the supernatant containing the baculovirus was collected. The GSTEGFR protein was purified using large cultures of Sf9 cells infected with stock virus. After an appropriate period of time, the cells were collected and lysed. The GSTEGFR was then purified from the lysate on Glutathione-Sepharose columns (as described by Amersham Biosciences, Buckinghamshire, United Kingdom).

The EGFR substrate was prepared by biotinylating poly-GluTyr (128 mg) (Sigma, St. Louis, Mo.) in a 1×PBS buffer incubated together with a 12-fold molar excess of Sulfo-NHS-LC-Biotin on ice for at least 2 hrs. The free biotin was separated from the biotinylated polyGluTyr on a gel filtration column.

A mixture of a 10× kinase buffer (500 mM Tris at pH 8.0, 100 mM Magnesium Chloride and 1 mM Sodium Vanadate), DTT (1 mM final from 500 mM stock), ATP (5 µM final from 10 mM stock), biotinylated polyGluTyr (10 µg/µL stock), γ-$^{33}$P ATP (10 µCi/µL stock) and water was added to each well (90 µL/well) of a Streptavidin Flashplate (Perkin Elmer, Wellesley, Mass.).

Test compound in 100% DMSO (2 µL) was added to the appropriate wells. Diluted GSTEGFR (1:300 dilution in 50 mM Tris at pH 8.0 and 0.1% bovine serum albumin) (10 µL) was added to the wells to initiate the reactions.

The plates were incubated at 30° C. for 1 hr with shaking. The reacted contents were removed and the plates were sequentially washed three times with a 1×PBS stop buffer (300 µL without Magnesium and Calcium) and 100 mM EDTA. After the final wash, the same stop buffer (200 µL) was added to the wells. The plates were then sealed and read on the TopCount scintillation counter.

Test compounds were assayed in triplicate at 16 concentrations at half-log dilutions starting at 200 uM. A maximum and minimum signal for the assay was determined on each plate. The percent inhibition of a test compound was calculated according to the formula $$\left[\frac{(\text{max signal} - \text{test compound})}{(\text{max signal} - \text{min signal})}\right](100) = \% \text{ inhibition}$$

For a series of test concentrations, the IC$_{50}$ was derived by graphing percent inhibition against the log of the concentrations tested for a given compound. The percent inhibition results are shown in Table 1 at a test concentration of 2 µM. For those compounds with an IC$_{50}$, the IC$_{50}$ value is shown in parentheses.

TABLE 1

| EGFR Inhibition (%) | |
|---|---|
| Cpd | IC$_{50}$ |
| 1 | 0.04902 |
| 2 | 0.01237 |
| 3 | 0.02982 |
| 4 | 0.01646 |
| 5 | 0.008204 |
| 6 | 0.01564 |
| 7 | 0.03115 |
| 8 | 0.02648 |
| 9 | 0.009768 |
| 10 | 0.05292 |

Example 2

HER2 Screening Assay

A kinase reaction mixture was prepared containing 50 mM Tris-HCl pH=8, 10 mM MgCl$_2$, 0.1 mM Na$_3$PO$_4$, 1 mM DTT, 10 µM ATP, 0.025 µM biotinylated histone-H1 peptide substrate and 0.2 µCuries per well $^{33P}$-γ-ATP (2000-3000 Ci/mmol). 70 µL of the kinase reaction mixture was dispensed into the well of a streptavidin coated FlashPlate™ (Cat. # SMP103, NEN, Boston, Mass.).

Test compound stock in 100% DMSO (1 µL) was added to the wells resulting in a final concentration of 1% DMSO in the reaction with a 100 µL final reaction volume. Each enzyme was diluted in 50 mM Tris-HCl pH=8.0, 0.1% BSA and 30 µL was added to each well to initiate the reaction. The reaction was incubated for one hour at 30° C. At the end of the 1 hr incubation, the reaction was terminated by aspirating the mixture from the plate and washing the wells twice with PBS containing 100 mM EDTA. The biotinylated peptide substrate became immobilized on the Flashplate™ and the incorporation of $^{33}$P-γ-ATP was measured by reading the plate on a scintillation counter. Inhibition of the enzymatic activity was measured by observing a reduced amount of $^{33}$P-γ-ATP incorporated into the immobilized peptide.

The HER2 construct consisted of a fusion of GST (Glutathione-S-Transferase), HIS6 Thrombin and the nucleotides encoding amino acids 679 to 1255 of HER-2 (Accession number M11730) (Proqinase, Freiburg, Germany). The assay used 200 ng of the N-terminal biotinylated peptide biotin-poly(GT) 4:1 (HER2) per well.

A maximum and minimum signal for the assay was determined on each plate. The percent inhibition of a test compound was calculated according to the formula:

$$\left[\frac{(\text{max signal} - \text{test compound})}{(\text{max signal} - \text{min signal})}\right](100) = \% \text{ inhibition}$$

For a series of test concentrations, the $IC_{50}$ was derived by graphing percent inhibition against the log of the concentrations tested for a given compound with results shown in Table 2.

TABLE 2

Her-2 $IC_{50}$ (µM)

| Cpd | $IC_{50}$ |
|-----|-----------|
| 1 | 0.1183 |
| 2 | 0.08357 |
| 3 | 0.01833 |
| 4 | 0.0066 |
| 5 | 0.0024 |
| 6 | 0.008399 |
| 7 | 0.07217 |
| 8 | 0.03884 |
| 9 | 0.008373 |
| 10 | 0.01985 |

Example 3

Cell Proliferation Inhibition Assay

The ability of a test compound to inhibit unregulated cell proliferation may be determined by measuring incorporation of $^{14}C$-labelled thymidine into newly synthesized DNA within cell lines derived from carcinomas originating from several tissues. Accordingly, the anti-proliferative effect of a compound on cells with a variety of phenotypes may be determined.

Carcinoma cell lines were obtained from the American Type Culture Collection (ATCC) and include those such as N87 (ATCC Cat. #), SKBR3 breast carcinoma (ATCC Cat. #HTB-30) and BT474 breast carcinoma (ATCC Cat. #HTB-20)

The carcinoma cells are trypsinized and counted. The cells (3000-8000 count) are added to each well of a 96-well CytoStar tissue culture treated scintillating microplate (Amersham #RPNQ0160) in complete medium (100 µL) and the plate is then incubated in complete medium for 24 hrs at 37° C. in an inert atmosphere containing 5% $CO_2$. Test compound (1 µL) in 100% DMSO is added to the plate test-wells with DMSO only added to control-wells. The plate is incubated in complete medium for a second 24 hr period at 37° C. in an atmosphere containing 5% $CO_2$.

An aliquot of a solution of Methyl $^{14}C$-thymidine (56 mC/mmol) (NEN #NEC568 or Amersham #CFA532) and complete medium (20 µL to provide 0.2 µCi/well) is then added to each well and the plate is incubated for a third 24 hr period at 37° C. in an atmosphere containing 5% $CO_2$. The plate contents are then discarded, the plate is washed twice with PBS (200 µL) and then PBS (200 µL) is added to each well. The plate is sealed and the degree of methyl $^{14}C$-thymidine incorporation is quantified on a Packard Top Count.

TABLE 3

| | $IC_{50}$ (Mean)(µM) | | |
|-----|-----|-----|-----|
| Cpd | BT-474 | N87 | SK-BR-3 |
| 3 | 0.0485 | 0.3646 | 0.6909 |
| 4 | 0.0305 | 0.09052 | 0.1216 |
| 5 | 0.06303 | 0.1313 | 0.1484 |
| 9 | 0.01355 | 0.05837 | 0.05848 |

Example 4

In Vivo Models—Inhibition of Tumor Growth

The ability of a test compound to inhibit unregulated growth of human tumor cells in vivo may be evaluated by implanting human tumor cells into the hind flank of athymic mice, administering a test compound and then quantifying any change in tumor size.

Human melanoma A375 cells ($10^6$ count) (ATCC Cat. #CRL-1619) are implanted subcutaneously into the hind flank of female athymic mice (Charles River) and allowed to grow for 6-10 days. After a measurable tumor is established (as determined by baseline caliper measurement), the animal is administered an oral dose of the test compound (in 10% solutol) daily for a period of 30 days. Tumor size is measured every five days and the degree of inhibition is determined by comparing drug-treated animals to vehicle-treated animals.

Variations of this method are intended to include intraperitoneal injection or intravenous infusion as the route of administration and administration of the test compound either alone or in a combination therapy.

While the foregoing specification teaches the principles of the present invention, with examples provided for the purpose of illustration, it will be understood that the practice of the invention encompasses all of the usual variations, adaptations and modifications as come within the scope of the following claims and their equivalents.

Throughout this application, various publications are cited. The disclosure of these publications is hereby incorporated by reference into this application to describe more fully the state of the art to which this invention pertains.

What is claimed is:

1. A compound of Formula (I):

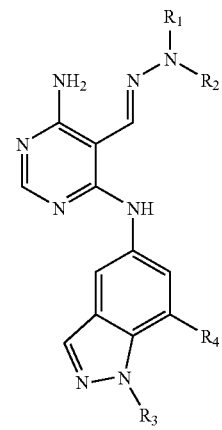

or a pharmaceutically acceptable salt thereof, wherein substituents on each side of the iminomethyl double bond in Formula (I) may be in the E or Z configuration; and wherein $R_1$ is hydrogen, $C_{1-6}$alkyl, trihalo $C_{1-6}$alkyl, $C_{3-6}$cycloalkyl, optionally substituted phenyl, or optionally substituted benzyl, wherein phenyl and the phenyl portion of benzyl is optionally substituted with one, two or three substituents selected from $C_{1-6}$alkyl, $C_{1-6}$alkoxy, hydroxy, amino, halogen, or trihalo $C_{1-6}$alkyl;

$R_2$ is hydrogen, or $C_{1-6}$alkyl;

or $R_1$ and $R_2$ taken together form an optionally substituted heterocyclic ring, wherein the heterocyclic ring is optionally substituted with one, two or three substituents selected from $C_{1-6}$alkyl, $C_{1-6}$alkoxy, $C_{1-6}$alkoxy-$C_{1-6}$alkyl, hydroxy-$C_{1-6}$alkyl, or trihalo $C_{1-6}$alkyl;

$R_3$ is benzyl optionally substituted with halo; and $R_4$ is hydrogen or halo.

2. A compound of claim 1, wherein $R_1$ is hydrogen, $C_{1-4}$alkyl, trihalo $C_{1-4}$alkyl, optionally substituted phenyl, or optionally substituted benzyl, wherein phenyl and the phenyl portion of benzyl is optionally substituted with one, two or three substituents selected from $C_{1-4}$alkyl, $C_{1-4}$alkoxy, hydroxy, amino, halogen, or trihalo $C_{1-4}$alkyl.

3. A compound of claim 1, wherein $R_1$ is hydrogen, $C_{1-4}$alkyl, trihalo $C_{1-4}$alkyl, or optionally substituted phenyl, wherein phenyl is optionally substituted with one, two or three substituents selected from $C_{1-4}$alkyl, $C_{1-4}$alkoxy, hydroxy, amino, halogen, or trihalo $C_{1-4}$alkyl.

4. A compound of claim 1, wherein $R_1$ is $C_{1-4}$alkyl, trihalo $C_{1-4}$alkyl, or phenyl substituted with $C_{1-4}$alkoxy.

5. A compound of claim 1, wherein $R_1$ and $R_2$ taken together form an optionally substituted heterocyclic ring, wherein the heterocyclic ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl.

6. A compound of claim 1, wherein $R_1$ and $R_2$ taken together form an optionally substituted pyrrolidinyl, morpholinyl, piperidinyl or piperazinyl ring, wherein the pyrrolidinyl, morpholinyl, piperidinyl or piperazinyl ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl.

7. A compound of claim 1, wherein $R_1$ and $R_2$ taken together form an optionally substituted pyrrolidinyl, morpholinyl, piperidinyl or piperazinyl ring, wherein the pyrrolidinyl or piperazinyl ring is optionally substituted with one substituent selected from $C_{1-4}$alkyl, $C_{1-4}$alkoxy-$C_{1-4}$alkyl, hydroxy-$C_{1-4}$alkyl.

8. A compound of claim 1, wherein $R_2$ is hydrogen.

9. A compound of claim 1, wherein $R_2$ is $C_{1-4}$alkyl.

10. A compound of claim 1, wherein $R_3$ is benzyl substituted with halo.

11. A compound of claim 1, wherein $R_4$ is hydrogen.

12. A compound of claim 1, wherein $R_1$ is hydrogen, $C_{1-4}$alkyl, trihalo $C_{1-4}$alkyl, optionally substituted phenyl, or optionally substituted benzyl, wherein phenyl and the phenyl portion of benzyl is optionally substituted with one, two or three substituents selected from $C_{1-4}$alkyl, $C_{1-4}$alkoxy, hydroxy, amino, halogen, or trihalo $C_{1-4}$alkyl;

$R_2$ is hydrogen, or $C_{1-4}$alkyl;

or $R_1$ and $R_2$ taken together form an optionally substituted heterocyclic ring, wherein the heterocyclic ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl;

$R_3$ is benzyl optionally substituted with halo; and $R_4$ is hydrogen.

13. A compound of claim 1, wherein $R_1$ is hydrogen, $C_{1-4}$alkyl, trihalo $C_{1-4}$alkyl, or optionally substituted phenyl, wherein phenyl is optionally substituted with one, two or three substituents selected from $C_{1-4}$alkyl, $C_{1-4}$alkoxy, hydroxy, amino, halogen, or trihalo $C_{1-4}$alkyl;

$R_2$ is hydrogen, or $C_{1-4}$alkyl;

or $R_1$ and $R_2$ taken together form an optionally substituted pyrrolidinyl, morpholinyl, piperidinyl or piperazinyl ring, wherein the pyrrolidinyl, morpholinyl, piperidinyl or piperazinyl ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl;

$R_3$ is benzyl substituted with halo; and $R_4$ is hydrogen.

14. A compound of claim 1, wherein $R_1$ is $C_{1-4}$alkyl, trihalo $C_{1-4}$alkyl, or phenyl substituted with $C_{1-4}$alkoxy;

$R_2$ is hydrogen, or $C_{1-4}$alkyl;

$R_3$ is benzyl substituted with halo; and $R_4$ is hydrogen.

15. A compound of claim 1, wherein $R_1$ and $R_2$ taken together form an optionally substituted pyrrolidinyl, morpholinyl, piperidinyl or piperazinyl ring, wherein the pyrrolidinyl, morpholinyl, piperidinyl or piperazinyl ring is optionally substituted with one, two or three substituents selected from $C_{1-4}$alkyl, $C_{1-4}$alkoxy, $C_{1-4}$alkoxy-$C_{1-4}$alkyl, hydroxy-$C_{1-4}$alkyl, or trihalo $C_{1-4}$alkyl;

$R_2$ is hydrogen, or $C_{1-4}$alkyl;

$R_3$ is benzyl substituted with halo; and $R_4$ is hydrogen.

16. A compound of claim 1, wherein $R_1$ and $R_2$ taken together form an optionally substituted pyrrolidinyl, morpholinyl, piperidinyl or piperazinyl ring, wherein the pyrrolidinyl or piperazinyl ring is optionally substituted with one substituent selected from $C_{1-4}$alkyl, $C_{1-4}$alkoxy-$C_{1-4}$alkyl, hydroxy-$C_{1-4}$alkyl;

$R_2$ is hydrogen, or $C_{1-4}$alkyl;
$R_3$ is benzyl substituted with halo; and
$R_4$ is hydrogen.

17. A compound selected from the group consisting of:
N-[1-(3-fluoro-benzyl)-1H-indazol-5-yl]-5-[(4-methoxy-phenyl)-hydrazonomethyl]-pyrimidine-4,6-diamine,
N-[1-(3-fluoro-benzyl)-1H-indazol-5-yl]-5-(methyl-hydrazonomethyl)-pyrimidine-4,6-diamine,
N-[1-(3-fluoro-benzyl)-1H-indazol-5-yl]-5-(piperidin-1-yliminomethyl)-pyrimidine-4,6-diamine,
N-[1-(3-fluoro-benzyl)-1H-indazol-5-yl]-5-(morpholin-4-yliminomethyl)-pyrimidine-4,6-diamine,
5-(dimethyl-hydrazonomethyl)-N-[1-(3-fluoro-benzyl)-1H-indazol-5-yl]-pyrimidine-4,6-diamine,
N-[1-(3-fluoro-benzyl)-1H-indazol-5-yl]-5-[(4-methyl-piperazin-1-ylimino)-methyl]-pyrimidine-4,6-diamine,
N-[1-(3-fluoro-benzyl)-1H-indazol-5-yl]-5-{[(2R)-2-methoxymethyl-pyrrolidin-1-ylimino]-methyl}-pyrimidine-4,6-diamine,
N-[1-(3-fluoro-benzyl)-1H-indazol-5-yl]-5-{[(2S)-2-methoxymethyl-pyrrolidin-1-ylimino]-methyl}-pyrimidine-4,6-diamine,
2-[4-({4-amino-6-[1-(3-fluoro-benzyl)-1H-indazol-5-ylamino]-pyrimidin-5-ylmethylene}-amino)-piperazin-1-yl]-ethanol, and
N-[1-(3-fluoro-benzyl)-1H-indazol-5-yl]-5-[(2,2,2-trifluoro-ethyl)-hydrazonomethyl]-pyrimidine-4,6-diamine.

18. A compound selected from the group consisting of:
N-[1-(3-fluoro-benzyl)-1H-indazol-5-yl]-5-(morpholin-4-yliminomethyl)-pyrimidine-4,6-diamine,
5-(dimethyl-hydrazonomethyl)-N-[1-(3-fluoro-benzyl)-1H-indazol-5-yl]-pyrimidine-4,6-diamine,
N-[1-(3-fluoro-benzyl)-1H-indazol-5-yl]-5-[(4-methyl-piperazin-1-ylimino)-methyl]-pyrimidine-4,6-diamine, and
2-[4-({4-amino-6-[1-(3-fluoro-benzyl)-1H-indazol-5-ylamino]-pyrimidin-5-ylmethylene}-amino)-piperazin-1-yl]-ethanol.

19. A method for ameliorating, treating or preventing breast cancer in a patient in need thereof comprising administering to the patient an effective amount of one or more compounds of claim 1.

20. The method of claim 19 wherein the effective amount of the compound of claim 1 is from about 0.001 mg/kg/day to about 300 mg/kg/day.

21. A process for preparing a compound of claim 1 comprising the steps of:

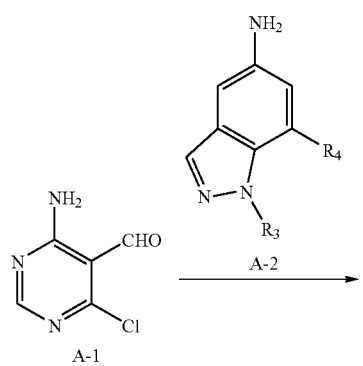

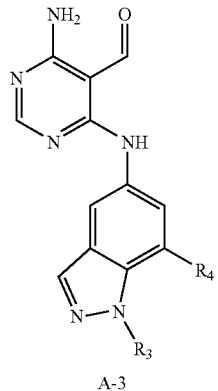

a. Compound A-1 is reacted with a Compound A-2 to provide a Compound A-3; and

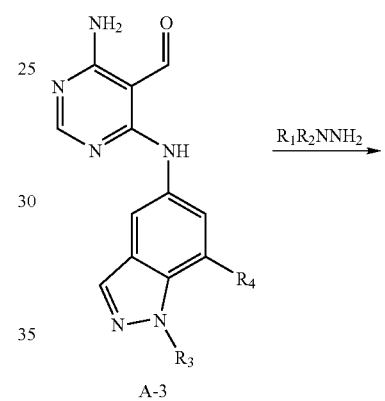

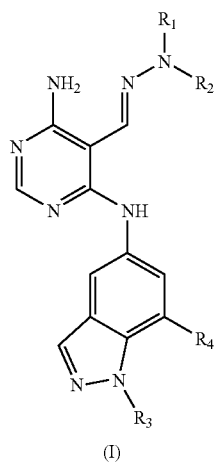

b. Compound A-3 is reacted with a hydrazine derivative $R_1R_2NNH$ to provide a Compound of Formula (I) (wherein substituents on each side of the iminomethyl double bond in Formula (I) may be in the E or Z configuration).

22. A pharmaceutical composition comprising the compound of claim 1.

* * * * *